United States Patent [19]
Kuma et al.

[11] Patent Number: 5,994,435
[45] Date of Patent: Nov. 30, 1999

[54] FLAME RETARDANT AND FLAME RETARDANT RESIN COMPOSITION FORMULATED WITH THE SAME

[75] Inventors: Kimitaka Kuma; Kenji Koyama; Nobuhiro Fujita; Takumi Kagawa, all of Shinnanyo; Fumio Okisaki, Yokkaichi; Keiji Itabashi, Shinnanyo, all of Japan

[73] Assignee: Tosoh Corporation, Yamaguchi-ken, Japan

[21] Appl. No.: 08/898,602

[22] Filed: Jul. 22, 1997

[30] Foreign Application Priority Data

Jul. 22, 1996 [JP] Japan .................................. 8-191979
Nov. 27, 1996 [JP] Japan .................................. 8-316651

[51] Int. Cl.$^6$ .............................. C08K 5/16; C09K 21/00
[52] U.S. Cl. ............................ 524/204; 252/609; 556/17; 556/26
[58] Field of Search ............................ 524/204; 556/17, 556/26; 252/609

[56] References Cited

U.S. PATENT DOCUMENTS 5,498,476   3/1996   Tucker et al. ................................ 524/140

OTHER PUBLICATIONS

"AMGARD®NK Flame Retardant", 2 pages from Albright & Wilson Americas (A Tennaco Company).

"Improved Intumescent Fire Retardant Systems", 9 pages by M.T. Huggard of Albright & Wilson Americas, Polymer Additives Group.

*Primary Examiner*—Veronica P. Hoke
*Attorney, Agent, or Firm*—Sughrue, Mion, Zinn, Macpeak & Seas, PLLC

[57] ABSTRACT

The subject of the invention is to provide a new high-performance flame retardant having excellent flame resistant effect and smoke-suppressing effect and generating no hazardous gas, and a new flame retardant resin-composition used it. As a means for solution, a flame retardant comprising ethylenediamine-containing zinc phosphate and other phosphorus-containing compound is formulated in amounts of 10 to 200 parts by weight to 100 parts by weight of resin.

24 Claims, 2 Drawing Sheets

FLAME RETARDANT AND FLAME RETARDANT RESIN COMPOSITION FORMULATED WITH THE SAME

BACKGROUND OF THE INVENTION

The present invention relates to a flame retardant comprising ethylenediamine-zinc phosphate and another phosphorus-containing compound and a flame retardant resin composition formulated with the same. The flame retardant resin composition formulated with the flame retardant of the invention is of high performance having excellent flame retardant and smoke suppressant properties and generating no hazardous gas, and is used extensively as a material for electronics, construction, transport and household materials, etc.

Although plastic materials are used in many industrial applications, because of their inflammability, flame retardants are formulated to plastic materials to afford the flame retardancy.

As the flame retardants used so far, there are phosphorus-based flame retardants such as a phosphoric ester, ammonium polyphosphate and red phosphorus, halogen-based flame retardants such as tetrabromobisphenol A, decabromodiphenyl oxide and chlorinated paraffin, inorganic flame retardants such as magnesium hydroxide, aluminum hydroxide, and the like. Thereamong, halogen-based flame retardants are excellent in the flame retardancy and are used widely.

However, resins formulated with halogen-based flame retardants have problems of releasing hazardous halogen-containing gas and generating much smoke on combustion. The generation of hazardous gas and smoke increases the risk of disaster on fire, resulting in injury or death, hence the safety of materials has become an important technology together with flame-retarding technology.

Moreover, the inorganic flame retardants release no hazardous gas during thermal decomposition and are materials excellent in the smoke suppressant effect, but they are not necessarily satisfactory in the point of flame retardancy.

Furthermore, ammonium polyphosphate is a material that generates no toxic gas during thermal decomposition, but it is the present situation that it is not necessarily satisfactory in the points of flame retardancy, water resistance, etc.

The invention was made in view of the problems aforementioned, and the purpose thereof is to propose a new high-performance flame retardant having excellent flame retardancy and smoke suppressant effect and generating no hazardous gas, and a new flame retardant resin composition using it.

As a result of diligent investigations for developing a flame retardant resin composition having excellent flame retardant and smoke suppressant properties and generating no hazardous gas, particularly putting an emphasis on the development of a high-performance flame retardant, the inventors have found that a flame retardant comprising ethylenediamine-zinc phosphate and another phosphorus containing compound is excellent in the flame retardancy, and a flame retardant resin composition formulated with this flame retardant is the high-performance flame retardant resin composition having excellent flame retardant and smoke suppressant properties and generating no hazardous gas, leading to the completion of the invention.

SUMMARY OF THE INVENTION

The invention provides a flame retardant comprising ethylenediamine-zinc phosphate and another phosphorus-containing compound, and a flame retardant resin composition formulated with 10 to 200 parts by weight of this flame retardant to 100 parts by weight of resin.

DETAILED DESCRIPTION OF THE INVENTION

In the following, the invention will be illustrated in detail.

In the invention, ethylenediamine-zinc phosphate is a compound between ethylenediamine and zinc phosphate, and, though not particularly restricted, for example, ethylenediamine-zinc phosphate having a general formula represented by $Zn_2P_2O_8C_2N_2H_{10}$ and a X-ray diffraction pattern including at least spacings shown in following Table 3, is useful.

TABLE 3

X-ray diffraction pattern of ethylenediamine-zinc phosphate

| Spacing d (Å) | 2θ | Relative intensity |
|---|---|---|
| 7.32 ± 0.50 | 12.1 | S~M |
| 5.66 ± 0.16 | 15.6 | M |
| 4.46 ± 0.10 | 19.9 | M |
| 4.10 ± 0.10 | 21.7 | W |
| 3.81 ± 0.08 | 23.3 | S~M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured with CuK α radiation
Relative intensity: VS: very strong, S: strong, M: medium, W: weak Ethylenediamine-zinc phosphate having a X-ray diffraction pattern including at least spacings shown in following Table 4, or the like, can be mentioned.

TABLE 4

X-ray diffraction pattern of ethylenediamine-zinc phosphate

| Spacing d (Å) | 2θ | Relative intensity |
|---|---|---|
| 6.89 ± 0.30 | 12.8 | VS |
| 6.66 ± 0.30 | 13.3 | S |
| 4.20 ± 0.10 | 21.1 | W |
| 4.09 ± 0.10 | 21.7 | S~M |
| 3.79 ± 0.08 | 23.4 | S |
| 3.38 ± 0.07 | 26.3 | S |
| 3.32 ± 0.05 | 26.8 | W |
| 3.14 ± 0.05 | 28.4 | M |
| 2.82 ± 0.04 | 31.7 | M |
| 2.74 ± 0.04 | 32.6 | S~M |
| 2.70 ± 0.04 | 33.1 | M |
| 2.60 ± 0.04 | 34.4 | W |

Figure 1:
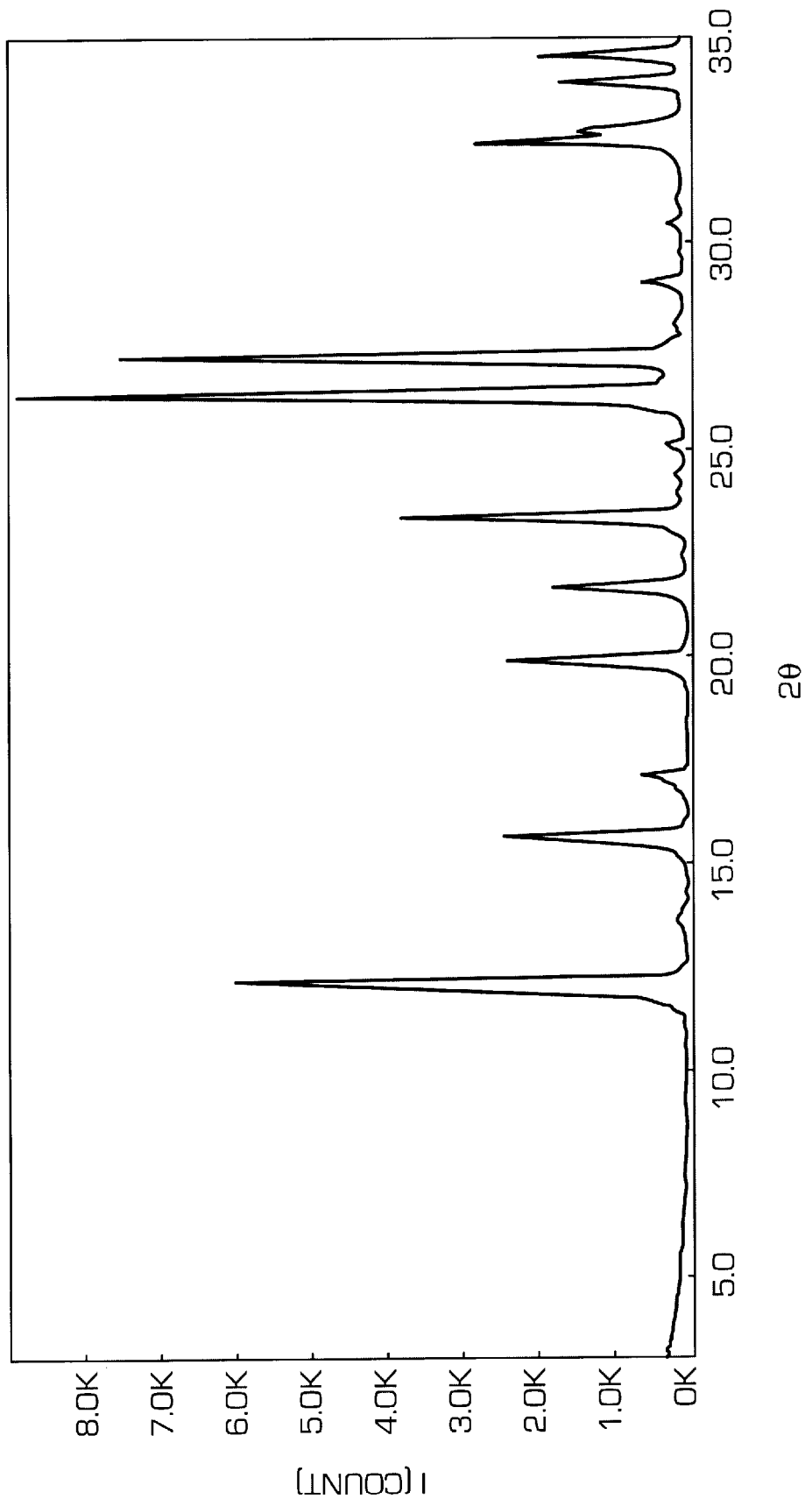
FIG. 1 is a X-ray diffraction pattern showing the crystalline structure of ethylenediamine-zinc phosphate obtained in Preparative example 1.

2θ: measured with CuK α radiation
Relative intensity: VS: very strong, S: strong, M: medium, W: weak Ethylenediamine-zinc phosphate having a general formula represented by $Zn_2P_2O_8C_2N_2H_{10}$ and a X-ray diffraction pattern including at least spacings shown in Table 3 above is a three dimensional open framework zinc phosphate. The structure is based on a network of $ZnO_4$ and $PO_4$ tetrahedra. The charge neutrality for $ZnPO_4^-$ is achieved by incorporation of the $H_3NC_2H_4NH_3^{2+}$ (R. H. Jones et. al., Studies in Surface Science and Catalysis, Zeolites and Related Microporous Materials, Vol. 84, p. 2229(1994), Elsevier Science B. V.). The X-ray diffraction pattern of ethylenediamine-zinc phosphate using CuK α radiation is shown in FIG. 1.

Figure 2:
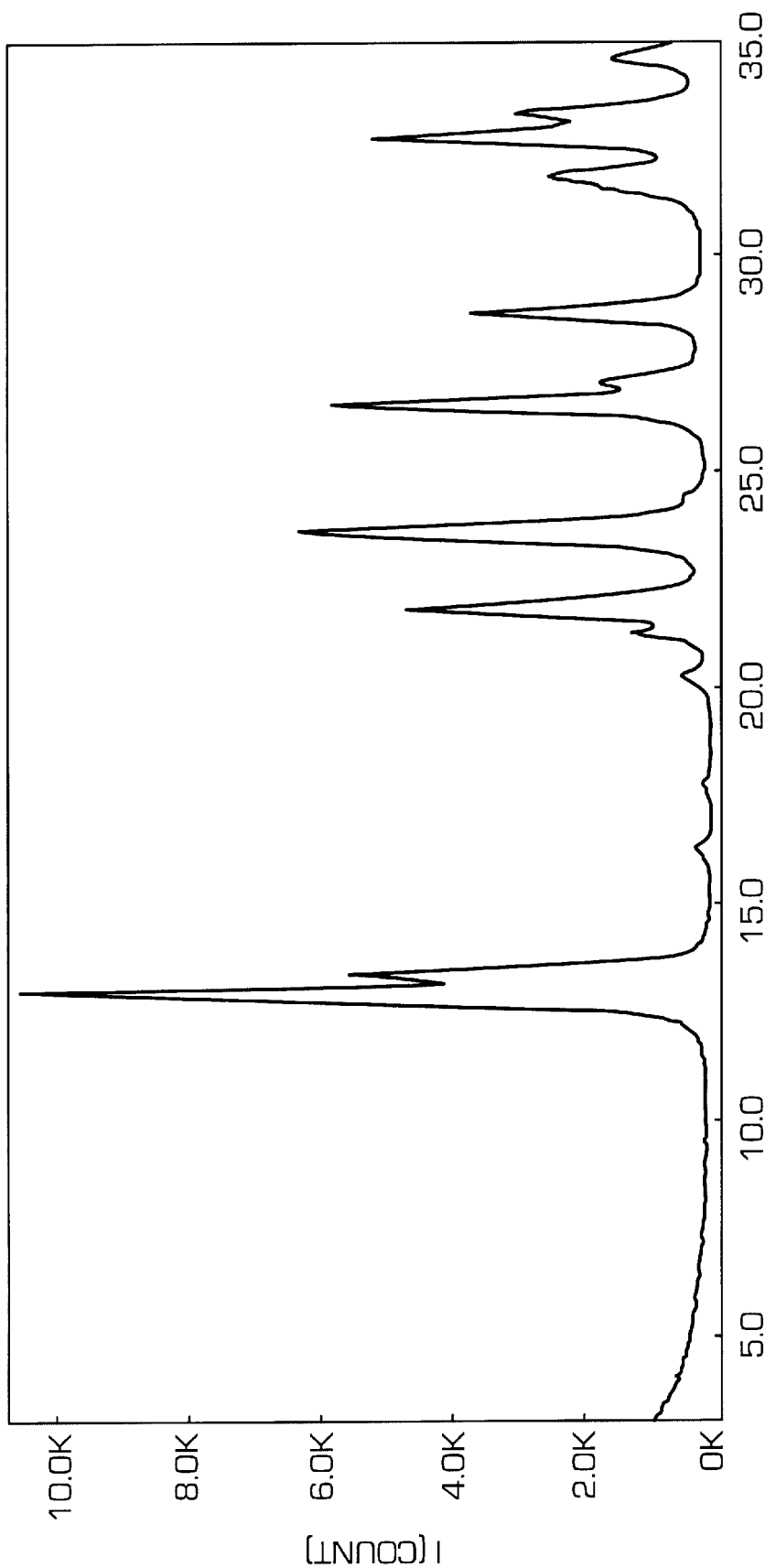
FIG. 2 is a X-ray diffraction pattern showing the crystalline structure of ethylenediamine-zinc phosphate obtained in Preparative example 2.

Moreover, although the detailed crystalline structure of ethylenediamine-zinc phosphate having a X-ray diffraction pattern including at least spacings shown in Table 4 above is not clear, the X-ray diffraction pattern measured using CuK α radiation becomes as shown in FIG. 2.

The decomposition temperature of ethylenediamine-containing zinc phosphate to be used in the invention is about 400° C., despite the boiling point of ethylenediamine being about 117° C. The decomposition temperatures of typical inorganic flame retardants are about 340° C. for magnesium hydroxide and about 200° C. for aluminum hydroxide. Namely, since the inventive ethylenediamine-zinc phosphate is a material excellent in the heat resistance over conventional inorganic flame retardants, it becomes possible to use it as a flame retardant also for the resins that require higher processing temperature and could not be adapted, hence it can be said to be a material with high versatility.

Besides, the BET specific surface area of ethylenediamine-zinc phosphate is 0.1 to 20 $m^2/g$ and the secondary particle diameter of ethylenediamine-containing zinc phosphate is around 20 µm or smaller.

Next, the process of producing ethylenediamine-zinc phosphate will be described, but, since the producing process is not particularly restricted, a preferable practical embodiment will be referred.

Ethylenediamine-zinc phosphate to be used in the invention is produced via each process of crystallization, filtration, washing, drying and pulverization of ethylenediamine-zinc phosphate.

In the case of ethylenediamine-zinc phosphate having a general formula represented by $Zn_2P_2O_8C_2N_2H_{10}$ and X-ray diffraction pattern including at least spacings shown in Table 3 above, the crystallization is performed by mixing an aqueous solution of zinc phosphate with an aqueous solution of ethylenediamine.

The aqueous solution of zinc phosphate is prepared by mixing a zinc compound with phosphoric acid in amounts of zinc/phosphorus ratio (molar ratio) of 1/10 to 2/5 and homogeneously dissolving the zinc compound. As the zinc compounds, metallic zinc, zinc hydroxide, Zinc oxide, zinc hydrogenphosphate, zinc dihydrogenphosphate or soluble zinc compounds such as zinc chloride, zinc nitrate and zinc sulfate, and the like are mentioned, but they are not particularly restricted. The concentration of phosphoric acid is not particularly restricted and the preparation may be performed at a concentration of 14 to 85 wt. %. The concentration of ethylenediamine is not particularly restricted and the preparation may be performed at a concentration of 5 to 100 wt. %.

Mixing of an aqueous solution of zinc phosphate with an aqueous solution of ethylenediamine may be performed in amounts of ethylenediamine/phosphorus ratio (molar ratio) of 2/1 to 1/2. As the mixing methods, such methods as adding an aqueous solution of ethylenediamine to an aqueous solution of zinc phosphate, adding an aqueous solution of zinc phosphate to an aqueous solution of ethylenediamine and adding an aqueous solution of zinc phosphate and ethylenediamine continuously into reactor are mentioned, but they are not particularly restricted. When mixing, it is preferable to perform it with stirring to make the contents inside of the reactor homogeneous. The temperature on mixing is enough to be 5 to 90° C. and the homogenizing time to be around 5 minutes to 3 days.

In the case of ethylenediamine-zinc phosphate having a X-ray diffraction pattern including at least spacings shown in Table 4 above, the crystallization is performed by mixing an aqueous solution of zinc salt with ethylenediamine to produce an aqueous solution of tris(ethylenediamine)zinc (II) and reacting the aqueous solution of tris (ethylenediamine)zinc(II) with phosphoric acid.

The process of producing an aqueous solution of tris (ethylenediamine)zinc(II) is not particularly restricted, but it can be obtained, for example, by mixing an aqueous solution of zinc salt with ethylenediamine at a molar ratio of 1/3 while stirring at a temperature of 5 to 90° C. The concentration of the aqueous solution of zinc salt is several mols/L, and, as the zinc salts, water-soluble salts such as zinc nitrate, zinc chloride and zinc sulfate, and the like are mentioned.

The reaction of an aqueous solution of tris (ethylenediamine) zinc(II) with phosphoric acid may be conducted at a mixing ratio of zinc/phosphoric acid of around 2/1 to 1/2 (molar ratio). When mixing, it is preferable to perform it with stirring to homogenize the contents inside of the reactor. The temperature on mixing is enough to be 5 to 90° C. and the homogenizing time to be around 5 minutes to 3 days.

The crystals of ethylenediamine-zinc phosphate are washed after solid-liquid separation. The method of solid-liquid separation is not particularly restricted and a Nutsche filter, rotary drum filter, filter press, horizontal band filter, etc. are exemplified. The quantity of washing water is not particularly restricted and it is only necessary to wash until unreacted phosphoric acid and ethylenediamine are removed.

Following this, drying of crystals of ethylenediamine-zinc phosphate is performed. The temperature on drying is not particularly restricted and drying may be performed at 60 to 250° C.

Further, the dried ethylenediamine-zinc phosphate is pulverized slightly. As the pulverizing methods, rotary crushers, hammer crushers, etc. are mentioned, but they are not particularly restricted.

Through the processes as mentioned above, ethylenediamine-zinc phosphate can be produced.

Next, explanation will be made about the flame retardant of the invention.

The flame retardant of the invention is a flame retardant comprising ethylenediamine-zinc phosphate and another phosphorus-containing compound. Although the detailed reason is unclear, there is a synergistic effect in the flame retardancy of ethylenediamine-zinc phosphate and another phosphorus-containing compound, and the inventive flame retardant composited ethylenediamine-zinc phosphate with another phosphorus-containing compound is of high performance, exhibiting very excellent flame retardancy.

In the invention, the formulating ratio of ethylenediamine-zinc phosphate to another phosphorus-containing compound is not particularly restricted, but the inventive one with a formulating ratio of ethylenediamine-zinc phosphate to another phosphorus compound of 1/4 to 4/1 at weight ratio exhibits very excellent flame retardancy, thus being particularly preferable.

The other phosphorus-containing compound to be used for the inventive flame retardant is not particularly restricted, if it is a phosphorus-containing compound other than ethylenediamine-zinc phosphate, but it may be one kind or two or more kinds selected from a group consisting of, for example, red phosphorus, ammonium polyphosphate, phosphoric ester, melamine phosphate and guanidine phosphate.

Further, the flame retardant resin composition of the invention will be explained.

The flame retardant resin composition of the invention is a composition formulated with 10 to 200 parts by weight, particularly preferably 30 to 120 parts by weight of the inventive flame retardant to 100 parts by weight of resin. When the formulation level of the inventive flame retardant is less than 10 parts by weight, the flame retardant effect is insufficient, which is unpreferable, and, when exceeding 200 parts by weight, the mechanical properties of the resin decrease in some cases, thus being unpreferable.

The resin can be used depending on the uses without being particularly restricted. For example, polyolefins being homopolymers or copolymers of olefinic monomers such as polyethylene, polypropylene, ethylene-propylene copolymer, ethylene-propylene-diene monomer terpolymer, ethylene-ethyl acrylate copolymer and ethylene-vinyl acetate copolymer, polystyrenes being homopolymers or copolymers mainly composed by vinyl aromatic monomers such as styrene homopolymer, rubber-modified polystyrene and graft polymer of rubber with acrylonitrile or (meth) acrylate and styrene, poly(meth)acrylic resins, polyesters such as poly(ethylene terephthalate), poly(butylene terephthalate) and polyarylate, polyamides such as 6-nylon, 6,6-nylon, 12-nylon, 46-nylon and aromatic polyamide, polyethers such as poly(phenylene ether), modified poly (phenylene ether) and polyoxymethylene, polycarbonate, styrene-conjugated diene copolymer, rubbers such as polybutadiene, polyisoprene, acrylonitrile-butadiene copolymer and polychloroprene, poly(vinyl chloride), and the like are mentioned. Also, thermosetting resins such as phenol resin, epoxy resin, vinyl ester resin, unsaturated polyester and polyurethane are mentioned. These resins may be used solely or by mixing a plurality of them.

As the method of formulating the inventive flame retardant to resin, the inventive one composited involving beforehand ethylenediamine-zinc phosphate with another phosphorus-containing compound may be formulated to resin, or they may be formulated each separately to resin. The compositing method is not particularly restricted, but it is only necessary to perform by wet or dry method with, for example, a ball mill or vibration mill using balls made of zirconia or urethane resin, a drum mixer, twin cylinder mixer, etc. The mixing time is enough to be around several hours to several tens of hours.

As the kneaders for formulating the flame retardant to resin, a mixing roll, sigma-type kneader, Banbury mixer, and screw type extruder are mentioned, but they are not particularly restricted and the formulation may be performed by a method adapted to the resin used.

Through the processes as mentioned above, the flame retardant resin composition of the invention can be produced.

The flame retardant resin composition of the invention has no troubles in any way in formulating with other additives, if need be. As the additives, other flame retardant, flame-retarding aid, plasticizer, lubricant, filler, antioxidant, heat stabilizer, crosslinking agent, crosslinking aid, antistatic agent, corolubilizing agent, light retardant agent, pigment, foaming agent, antimold agent, etc. are mentioned.

The inventive flame retardant comprising ethylenediamine-zinc phosphate and another phosphorus-containing compound is excellent in the flame retardancy, and the inventive flame retardant resin composition formulated with this is of high performance having excellent flame retardant and smoke suppressant properties and generating no hazardous gas.

In the following, the invention will be illustrated further concretely based on examples, but the invention is not confined to these.

Preparative Example 1
Preparation of Ethylenediamine-zinc Phosphate (1)

Into an an aqueous solution of phosphoric acid prepared by adding 327 g of 75% phosphoric acid to 700 g of water, 81.4 g of zinc oxide were dissolved with stirring to prepare an an aqueous solution of zinc phosphate.

An an aqueous solution of ethylenediamine prepared by adding 75 g of ethylenediamine to 658 g of water was added to said an aqueous solution of zinc phosphate, and the slurry was homogenized for 3 hours at 25° C. to crystallize out ethylenediamine-zinc phosphate. After crystallization, solids were separated from liquid by Nutsche filtration, washed with 3000 g of water, and dried for 16 hours at 110° C. to prepare ethylenediamine-zinc phosphate. The X-ray diffraction of ethylenediamine-zinc phosphate appeared at the locations shown in Table 3 above. Moreover, this X-ray diffraction pattern is shown in FIG. 1.

Preparative Example 2
Preparation of Ethylenediamine-zinc Phosphate (2)

Into an an aqueous solution of phosphoric acid prepared by adding 327 g of 75% phosphoric acid to 700 g of water, 81.4 g of zinc oxide were dissolved with stirring to prepare an an aqueous solution of zinc phosphate.

To an an aqueous solution of ethylenediamine prepared by adding 75 g of ethylenediamine to 658 g of water, said aqueous solution of zinc phosphate was added, and the slurry was homogenized for 1 hour at 30° C. to crystallize out ethylenediamine-zinc phosphate. After crystallization, solids were separated from liquid by Nutsche filtration, washed with 3000 g of water, and dried for 16 hours at 110° C. to prepare ethylenediamine-zinc phosphate. The X-ray diffraction of ethylenediamine-zinc phosphate appeared at the locations shown in Table 3 above.

Preparative Example 3
Preparation of Ethylenediamine-zinc Phosphate (3)

Into 540 g of water, 59.5 g of zinc nitrate.hexahydrate were dissolved, and, to this an aqueous solution of zinc nitrate, 36 g of ethylenediamine were added to prepare an aqueous solution of tris(ethylenediamine)zinc(II).

An an aqueous solution of phosphoric acid prepared by adding 23.1 g of 85% phosphoric acid to 180 g of water was added to said an aqueous solution of tris(ethylenediamine) zinc(II), and the slurry was homogenized for 1 hour at 30° C. to crystallize out ethylenediamine-zinc phosphate. After crystallization, solids were separated from liquid by Nutsche filtration, washed with 3000 g of water, and dried for 16 hours at 110° C. to prepare ethylenediamine-zinc phosphate. The X-ray diffraction of ethylenediamine-zinc phosphate appeared at the locations shown in Table 4 above. Moreover, this X-ray diffraction pattern is shown in FIG. 2.

Preparative Example 4
Preparations of Flame Retardant 1 through Flame Retardant 5

Ethylenediamine Zinc phosphate prepared in Preparative example 1 and ammonium polyphosphate (from Hoechst, trade name "HOSTAFLAM AP 462") as an other phosphorus-containing compound were mixed at weight ratios of 1:4, 1:2, 1:1, 2:1 and 4:1, respectively, and ball-milled for 16 hours using urethane resin balls to prepare flame retardant 1 through flame retardant 5.

Preparative Example 5
Preparations of Flame Retardant 6 through Flame Retardant 10

Ethylenediamine-zinc phosphate prepared in Preparative example 2 and red phosphorus (from Rin Kagaku, trade name "Nouvared 120") as an other phosphorus-containing compound were mixed at weight ratios of 1:4, 1:2, 1:1, 2:1 and 4:1, respectively, and composited by the same method as in Preparative example 4 to prepare flame retardant 6 through flame retardant 10.

Preparative Example 6
Preparation of Flame Retardant 11

Ethylenediamine-zinc phosphate prepared in Preparative example 3 and ammonium polyphosphate (from Hoechst, trade name "HOSTAFLAM AP 462") as an other phosphorus-containing compound were mixed at weight ratios of 1:1, and composited by the same method as in Preparative example 4 to prepare flame retardant 11.

Preparative Example 7
Preparation of Flame Retardant 12

Ethylenediamine-zinc phosphate prepared in Preparative example 1 and melamine phosphate (from Sanwa Chemical, trade name "MPP-2") as an other phosphorus-containing compound were mixed at a weight ratio of 1:3, and composited by the same method as in Preparative example 4 to prepare flame retardant 12.

Preparative Example 8
Preparation of Flame Retardant 13

Ethylenediamine-zinc phosphate prepared in Preparative example 1 and guanidine phosphate (from Sanwa Chemical, trade name "Apinon 301") as an other phosphorus-containing compound were mixed at a weight ratio of 1:2, and composited by the same method as in Preparative example 4 to prepare flame retardant 13.

EXAMPLE 1
Evaluation of Flame Retardancy (1)

Flame retardant resin composition was prepared by adding a fixed amount of flame retardant into ethylene-ethyl acrylate copolymer (from Nippon Oil, trade name Lextron EEA grade A1150) under roll-mixing at 150° C. The resultant formulation was molded with press at 180° C. and then cut to the required test specimen specifications.

The evaluations of flame retardancy were determined by limiting oxygen index according to JIS K7201 and Underwrites Laboratory vertical burn test (UL94, thickness of specimen ⅛ inch).

The formulation level of each flame retardant and the evaluation results of flame resistance of flame retardant resin compositions are shown Table 5.

TABLE 5

Evaluation of flame retardancy (Example 1)

| Flame retardant | Formulation level (phr) | Oxygen index | UL94 |
| --- | --- | --- | --- |
| Flame retardant 1 | 60 | 35 | V0 |
| Flame retardant 2 | 60 | 36 | V0 |

TABLE 5-continued

Evaluation of flame retardancy (Example 1)

| Flame retardant | Formulation level (phr) | Oxygen index | UL94 |
| --- | --- | --- | --- |
|  | 50 | 31 | V0 |
|  | 48 | 32 | V0 |
|  | 46 | 31 | V0 |
| Flame retardant 3 | 60 | 32 | V0 |
|  | 80 | 34 | V0 |
| Flame retardant 4 | 60 | 29 | V1 |
| Flame retardant 5 | 60 | 25 | HB |
| Flame retardant 6 | 60 | 25 | HB |
| Flame retardant 7 | 60 | 26 | HB |
| Flame retardant 8 | 60 | 28 | V0 |
| Flame retardant 9 | 60 | 29 | V0 |
| Flame retardant 10 | 60 | 31 | V0 |
|  | 50 | 28 | V0 |
|  | 40 | 33 | V0 |
|  | 38 | 28 | V0 |
|  | 36 | 28 | V0 |
|  | 34 | 26 | V1 |
| Flame retardant 11 | 60 | 31 | V0 |
| Flame retardant 12 | 120 | 33 | V0 |
| Flame retardant 13 | 90 | 33 | V0 |

Resin: ethylene-ethyl acrylate copolymer

EXAMPLE 2
Evaluation of Flame Retardancy (2)

Flame retardant resin composition was prepared by adding a fixed amount of flame retardant into low-density polyethylene (from Tosoh, trade name Petrocene 202) under roll-mixing at 105° C. The resultant formulation was molded with press at 150° C. and then cut to the required that specimen specifications.

The evaluations of flame retardancy were performed by the same method as in Example 1.

The formulation level of each flame retardancy and the evaluation results of flame resistance of flame retardant resin compositions are shown in Table 6.

TABLE 6

Evaluation of flame retardancy (Example 2)

| Flame retardant | Formulation level (phr) | Oxygen index | UL94 |
| --- | --- | --- | --- |
| Flame retardant 1 | 60 | 30 | V0 |
| Flame retardant 2 | 60 | 33 | V0 |
|  | 56 | 29 | V2 |
| Flame retardant 3 | 60 | 31 | V0 |
| Flame retardant 4 | 60 | 25 | V1 |
| Flame retardant 5 | 60 | 25 | HB |
| Flame retardant 6 | 60 | 25 | HB |
| Flame retardant 7 | 60 | 26 | HB |
| Flame retardant 8 | 60 | 28 | V0 |
| Flame retardant 9 | 60 | 29 | V0 |
| Flame retardant 10 | 60 | 31 | V0 |
|  | 50 | 26 | V0 |
|  | 48 | 26 | V0 |
|  | 46 | 25 | V2 |

Resin: low-density polyethylene

EXAMPLE 3
Evaluation of Smoke Density

Flame retardant resin composition was prepared by the same method as in Example 2.

Optical density measurements on the smoke evolved from burning samples were carried out using a NBS-type Smoke Box.

The formulation level of each flame retardant and smoke density of flame retardant resin compositions are shown in Table 7.

TABLE 7

Evaluation of smoke density (Example 3)

| Flame retardant | Formulation level (phr) | Smoke density |
|---|---|---|
| Flame retardant 2 | 60 | 91 |
| Flame retardant 3 | 60 | 34 |
| Flame retardant 10 | 48 | 190 |

Resin: low-density polyethylene

Comparative Example 1

Evaluation of Flame Retardancy

Flame retardant resin composition was prepared by the same method as in Example 2 and the evaluations of flame retardancy were performed by the same method as in Example 1.

The formulation level of each flame retardant and the evaluation results of flame resistance of flame retardant resin compositions are shown in Table 8.

TABLE 8

Evaluation of flame retardancy (Comparative example 1)

Flame retardant (phr)

| ZP | Red phosphorus | APP | Hydro mag | Oxygen index | UL94 |
|---|---|---|---|---|---|
| 60 | — | — | — | 23 | HB |
| 100 | — | — | — | 24 | HB |
| — | 60 | — | — | 23 | HB |
| — | — | 60 | — | 26 | V2 |
| — | — | — | 100 | 24 | HB |
| — | — | — | 30 | 22 | V2 |
| 30 | — | — | 30 | 22 | HB |

Resin: low-density polyethylene
ZP: Abbreviation of ethylenediamine zinc phosphate (prepared in Preparative example 1)
Red phosphorus: from Rin Kagaku, trade name "Nouvared 120"
APP: Abbreviation of ammonium polyphosphate from Hoechst, trade name "HOSTAFLAM AP 462"
Hydro mag: Abbreviation of magnesium hydroxide, from Kyowa Kagaku, trade name "Xismer-5A-1"

Comparative Example 2

Evaluation of Smoke Density

Flame retardant resin composition was prepared by the same method as in Example 2 and the evaluations of smoke density were performed by the same method as in Example 3.

The formulation level of each flame retardant and the smoke density of flame resistant resin compositions are shown in Table 9.

TABLE 9

Evaluation of smoke density (Comparative example 2)

Flame retardant (phr)

| DBDE | $Sb_2O_3$ | APP | Hydro mag | EDAP | Smoke density |
|---|---|---|---|---|---|
| 30 | 10 | — | — | — | 385 |
| — | — | 30 | 150 | — | 107 |
| — | — | — | — | 67 | 184 |

Resin: low-density polyethylene
DBDE: Abbreviation of decabromodiphenyl oxide, from Tosoh, trade name "Flame Cut 110R"
$Sb_2O_3$: From Tosoh, trade name "Flame Cut 610R"
APP: Abbreviation of ammonium polyphosphate from Hoechst, trade name "HOSTAFLAM AP 462"
Hydro mag: Abbreviation of magnesium hydroxide, from Kyowa Kagaku, trade name "Xismer-5A-1"
EDAP: Abbreviation of ethylenediamine-containing zinc phosphate, from Albright & Wilson Americas, trade name "Amgard NK"

Besides, this evaluation of smoke density was implemented at a minimum formulation level where the flame retardancy became V0 judgment according to UL 94 V for each flame retardant. It can be seen that the inventive flame retardant is a material excellent in the smoke suppressant effect compared with other flame retardants.

What is claimed is:

1. A flame retardant comprising the compound ethylenediamine-zinc phosphate and another phosphorus-containing compound which, in combination with the ethylenediamine-zinc phosphate, improves flame retardancy.

2. The flame retardant of claim 1, wherein the general formula of the ethylenediamine-zinc phosphate is represented by $Zn_2P_2O_8C_2N_2H_{10}$ and the X-ray diffraction pattern of the ethylenediamine-zinc phosphate includes at least spacings shown in Table 1

TABLE 1

X-ray diffraction pattern of ethylenediamine-zinc phosphate

| Spacing d (Å) | 2 θ | Relative intensity |
|---|---|---|
| 7.32 ± 0.50 | 12.1 | S~M |
| 5.66 ± 0.50 | 15.6 | M |
| 4.46 ± 0.10 | 19.9 | M |
| 4.10 ± 0.10 | 21.7 | W |
| 3.81 ± 0.08 | 23.2 | S~M |
| 3.39 ± 0.07 | 26.2 | VS |
| 3.28 ± 0.05 | 27.2 | S |
| 2.76 ± 0.04 | 32.4 | W |
| 2.73 ± 0.04 | 32.8 | W |
| 2.65 ± 0.04 | 33.8 | W |
| 2.60 ± 0.04 | 34.5 | W |
| 2.31 ± 0.04 | 38.9 | W |
| 2.21 ± 0.04 | 40.9 | W |

2θ: measured with CuK α radiation
Relative intensity: VS: very strong, S: strong, M: medium, W: weak.

3. The flame retardant of claim 1, wherein the X-ray diffraction pattern of the ethylenediamine-zinc phosphate includes at least spacings shown in Table 2

TABLE 2

X-ray diffraction pattern of ethylenediamine-zinc phosphate

| Spacing d (Å) | 2 θ | Relative intensity |
|---|---|---|
| 6.89 ± 0.30 | 12.8 | VS |
| 6.66 ± 0.30 | 13.3 | S |
| 4.20 ± 0.10 | 21.1 | W |
| 4.09 ± 0.10 | 21.7 | S~M |
| 3.79 ± 0.08 | 23.4 | S |
| 3.38 ± 0.07 | 26.3 | S |
| 3.32 ± 0.05 | 26.8 | W |
| 3.14 ± 0.05 | 28.4 | M |
| 2.82 ± 0.04 | 31.7 | M |
| 2.74 ± 0.04 | 32.6 | S~M |
| 2.70 ± 0.04 | 33.1 | M |
| 2.60 ± 0.04 | 34.4 | W |

2θ: measured with CuK α radiation
Relative intensity: VS: very strong, S: strong, M: medium, W: weak.

4. The flame retardant of claim 1, wherein the formulating ratio of the ethylenediamine-zinc phosphate to the another phosphorous-containing compound is within a range of 1/4 to 4/1.

5. The flame retardant of claim 2, wherein the formulating ratio of the ethylenediamine-zinc phosphate to the another phosphorous-containing compound is within the range of 1/4 to 4/1.

6. The flame retardant of claim 3, wherein the formulating ratio of the ethylenediamine-zinc phosphate to the another phosphorous-containing compound is within the range of 1/4 to 4/1.

7. The flame retardant of claim 1, wherein the another phosphorous-containing compound is one or more compounds selected from the group consisting of red phosphorous, ammonium polyphosphate, phosphoric ester, melamine phosphate and guanidine phosphate.

8. The flame retardant of claim 2, wherein the another phosphorous-containing compound is one or more compounds selected from the group consisting of red phosphorous, ammonium polyphosphate, phosphoric ester, melamine phosphate and guanidine phosphate.

9. The flame retardant of claim 3, wherein the another phosphorous-containing compound is one or more compounds selected from the group consisting of red phosphorous, ammonium polyphosphate, phosphoric ester, melamine phosphate and guanidine phosphate.

10. The flame retardant of claim 4, wherein the another phosphorous-containing compound is one or more compounds selected from the group consisting of red phosphorous, ammonium polyphosphate, phosphoric ester, melamine phosphate and guanidine phosphate.

11. The flame retardant of claim 5, wherein the another phosphorous-containing compound is one or more compounds selected from the group consisting of red phosphorous, ammonium polyphosphate, phosphoric ester, melamine phosphate and guanidine phosphate.

12. The flame retardant of claim 6, wherein the another phosphorous-containing compound is one or more compounds selected from the group consisting of red phosphorous, ammonium polyphosphate, phosphoric ester, melamine phosphate and guanidine phosphate.

13. A flame retardant resin composition formulated with 10 to 200 parts by weight of the flame retardant of claim 1 to 100 parts by weight of resin.

14. The flame retardant resin composition of claim 13, wherein the formulating ratio of the ethylenediamine-zinc phosphate to the another phosphorous-containing compound is within the range of 1/4 to 4/1.

15. The flame retardant resin composition of claim 13, wherein the another phosphorous-containing compound is one or more compounds selected from the group consisting of red phosphorous, ammonium polyphosphate, phosphoric ester, melamine phosphate and guanidine phosphate.

16. The flame retardant resin composition of claim 14, wherein the another phosphorous-containing compound is one or more compounds selected from the group consisting of red phosphorous, ammonium polyphosphate, phosphoric ester, melamine phosphate and guanidine phosphate.

17. A flame retardant resin composition formulated with 10 to 200 parts by weight of the flame retardant of claim 2 to 100 parts by weight of resin.

18. The flame retardant resin composition of claim 17, wherein the formulating ratio of the ethylenediamine-zinc phosphate to the another phosphorous-containing compound is within the range of 1/4 to 4/1.

19. The flame retardant resin composition of claim 17, wherein the another phosphorous-containing compound is one or more compounds selected from the group consisting of red phosphorous, ammonium polyphosphate, phosphoric ester, melamine phosphate and guanidine phosphate.

20. The flame retardant resin composition of claim 18, wherein the another phosphorous-containing compound is one or more compounds selected from the group consisting of red phosphorous, ammonium polyphosphate, phosphoric ester, melamine phosphate and guanidine phosphate.

21. A flame retardant resin composition formulated with 10 to 200 parts by weight of the flame retardant of claim 3 to 100 parts by weight of resin.

22. The flame retardant resin composition of claim 21, wherein the formulating ratio of the ethylenediamine-zinc phosphate to the another phosphorous-containing compound is within the range of 1/4 to 4/1.

23. The flame retardant resin composition of claim 21, wherein the another phosphorous-containing compound is one or more compounds selected from the group consisting of red phosphorous, ammonium polyphosphate, phosphoric ester, melamine phosphate and guanidine phosphate.

24. The flame retardant resin composition of claim 22, wherein the another phosphorous-containing compound is one or more compounds selected from the group consisting of red phosphorous, ammonium polyphosphate, phosphoric ester, melamine phosphate and guanidine phosphate.

* * * * *